United States Patent
Tark (10) Patent No.: US 10,702,457 B2
(45) Date of Patent: Jul. 7, 2020

(54) METHOD FOR PREPARING VEGETABLE OIL EMULSION BY ULTRASONICATION

(71) Applicant: ADHOME CO., LTD., Gyeonggi-do (KR)

(72) Inventor: Jae Hwa Tark, Seoul (KR)

(73) Assignee: ADHOME CO., LTD., Gyeonggi-Do (KR)

( * ) Notice: Subject to any disclaimer, the term of this patent is extended or adjusted under 35 U.S.C. 154(b) by 228 days.

(21) Appl. No.: 15/927,358

(22) Filed: Mar. 21, 2018

(65) Prior Publication Data
US 2018/0296448 A1 Oct. 18, 2018

(30) Foreign Application Priority Data
Apr. 13, 2017 (KR) .................. 10-2017-0047785

(51) Int. Cl.
| | | |
|---|---|---|
| *A61K 8/06* | (2006.01) | |
| *A61K 8/92* | (2006.01) | |
| *A23L 5/30* | (2016.01) | |
| *A61K 36/53* | (2006.01) | |
| *A61Q 19/00* | (2006.01) | |
| *A61K 8/9789* | (2017.01) | |
| *A23L 27/12* | (2016.01) | |

(52) U.S. Cl.
CPC ............... *A61K 8/062* (2013.01); *A23L 5/32* (2016.08); *A23L 27/12* (2016.08); *A23L 27/13* (2016.08); *A61K 8/922* (2013.01); *A61K 8/9789* (2017.08); *A61K 36/53* (2013.01); *A61Q 19/00* (2013.01); *A61K 2800/10* (2013.01); *A61K 2800/82* (2013.01)

(58) Field of Classification Search
CPC ....... A61K 8/062; A61K 8/922; A61K 8/9789; A61K 36/53; A23L 5/32; A23L 27/12; A23L 27/13
See application file for complete search history.

(56) References Cited

U.S. PATENT DOCUMENTS
2005/0214432 A1   9/2005 Belmar et al.

FOREIGN PATENT DOCUMENTS
| KR | 1020000068575 | 11/2000 |
| KR | 1020140097932 | 8/2014 |
| KR | 1020150116374 | 10/2015 |

OTHER PUBLICATIONS

KR1020140097932 machine translation (Year: 2014).*

* cited by examiner

*Primary Examiner* — Edward J Cain
(74) *Attorney, Agent, or Firm* — IPLA P.A.; James E. Bame (57) ABSTRACT

Provided is a method for preparing a vegetable oil emulsion including mixing water with a vegetable oil to provide a first mixture (a), and applying ultrasonic waves with a frequency of 25 to 70 kHz to the first mixture to solubilize the first mixture (b). Through treatment of ultrasonic waves with a certain frequency, the method for preparing a vegetable oil emulsion according to the present invention has advantages of significantly easily converting various herbal oils into aqueous emulsions at a high yield, significantly preventing layer-separation between oils and water for a long time, and being widely applicable to a variety of herbal oils.

4 Claims, 7 Drawing Sheets

METHOD FOR PREPARING VEGETABLE OIL EMULSION BY ULTRASONICATION

CROSS REFERENCE

This application claims foreign priority under Paris Convention to Korean Patent Application No. 10-2017-0047785, filed 13 Apr. 2017, with the Korean Intellectual Property Office.

BACKGROUND

The present invention relates to a method for preparing a vegetable oil emulsion by ultrasonication, and more specifically, to a method for preparing a vegetable oil emulsion that can improve emulsion conversion of an oil and significantly prevent layer-separation between the oil and deionized water.

Owing to unique ingredients omitting fragrances, various vegetable oils such as herbal oils have various efficacies such as stress relief, psychological sedation, skin soothing, odor removal, strengthening of the body's immune system, and physical (body) stabilization.

Meanwhile, these vegetable oils are utilized as massage or fragrant oils which are not stock (crude) oils extracted from plants but are dilutions of the stock oils in various ingredients.

In addition, these herbal oils may be used for cosmetics or diffusers that emit fragrances into the air. In order for herbal oils to be used for cosmetics or diffusers, the process involving mixing water such as deionized water with vegetable oils and converting the mixture into an emulsion is required.

However, it is extremely difficult to homogeneously mix vegetable oils with water due to their physical and chemical properties and, even if the vegetable oils are mixed with water, the oils and water may undergo layer-separation within a short time.

Meanwhile, the following Patent Document 1 discloses a method for preparing an aqueous emulsion by mixing retinispora oil extracted from retinispora (*Chamaecyparis pisifera*) with water and then subjecting the mixture to ultrasonication. However, when the ultrasonication of Patent Document 1 is used, the emulsification proportion of the retinispora oil is low, and when the method is applied to emulsification of various herbal oils, there are problems that almost no aqueous emulsification occurs in most herbal oils or the herbal oils are immediately layer-separated.

Accordingly, there is an urgent need for development of a novel method for preparing a vegetable oil emulsion that can convert herbal oils through ultrasonication into aqueous emulsions where the herbal oils are homogenously mixed with water, prevent layer-separation between the oils and water for a long time and can be widely applied for general use to a variety of herbal oils.

SUMMARY OF THE INVENTION

Therefore, the present invention has been made in view of the above problems, and it is one object of the present invention to provide a method for preparing a vegetable oil emulsion that can be widely applied to a variety of herbal oils, has a high oil-emulsion conversion ratio and can significantly prevent layer-separation between the oils and water for a long time.

In accordance with the present invention, the above and other objects can be accomplished by the provision of a method for preparing a vegetable oil emulsion including mixing water with a vegetable oil to provide a first mixture (a), and applying ultrasonic waves with a frequency of 25 to 70 kHz to the first mixture to solubilize the first mixture (b).

The method may further include removing floating residues (c) after step (b).

Application of ultrasonic waves in step (b) may be carried out while regularly changing an oscillation frequency in order to prevent resonance.

The first mixture may be obtained by mixing the vegetable oil in an amount of 0.1 to 30 mL per 1 L of water.

Step (b) may be carried out by maintaining the temperature of the first mixture at 20 to 80° C.

Step (b) may be carried out by for 10 minutes to 8 hours.

The vegetable oil may include one or more selected from the group consisting of lavender oil, lemongrass oil, rosemary oil, rose oil, citronella oil, lemon oil, bergamot oil, cedarwood oil, tea tree oil, peppermint oil, eucalyptus oil, anise oil, juniper berry oil, carrot seed oil, clary sage oil, clove bud oil, mandarin oil, myrrh oil, basil oil, cypress oil, sandalwood oil, sweet orange oil, spearmint oil, cinnamon oil, ylang ylang oil, jasmine oil, geranium oil, chamomile oil, neroli oil, lime oil, rose geranium oil, rosewood oil, marjoram oil, thyme oil, pine oil, palmarosa oil, fennel oil, petitgrain oil, patchouli oil, frankincense oil or a combination thereof.

Through treatment with ultrasonic waves with a certain frequency, the method for preparing a vegetable oil emulsion according to the present invention has advantages of significantly easily converting various herbal oils into aqueous emulsions at a high yield, significantly preventing layer-separation between the oils and water for a long time, and being broadly applicable to a variety of herbal oils.

BRIEF DESCRIPTION OF DRAWINGS

The above and other objects, features and other advantages of the present invention will be more clearly understood from the following detailed description taken in conjunction with the accompanying drawings, in which.

DETAILED DESCRIPTION OF THE INVENTION

Prior to describing the present invention in more detail, it should be understood that terms or words used in the disclosure and claims are not limited to ordinary or dictionary meanings and are not construed as limited to ordinary or dictionary terms and correspond to meanings and definitions that suit the technical concepts of the present invention under the principle that the meanings of the terms can be suitably defined in order to describe the present invention in the best manner. Accordingly, embodiments described in the disclosure are merely provided as preferred examples and do not represent all technical concepts of the present invention. Therefore, it should be understood that there may be various equivalents and modifications that can replace the examples at the filing time of the present invention.

The present invention is related to a method for preparing a vegetable oil emulsion that is capable of easily preparing emulsions at a high yield such that various vegetable oils such as herbal oils are mixed with water and can be stably maintained in a homogeneous emulsion for a long time.

As used herein, the term "emulsion" is construed as meaning a solution wherein two or more substances that are immiscible with one another due to their physical or chemical properties are homogenously mixed, for example, a solution wherein water and an oil are homogenously mixed.

Figure 1:
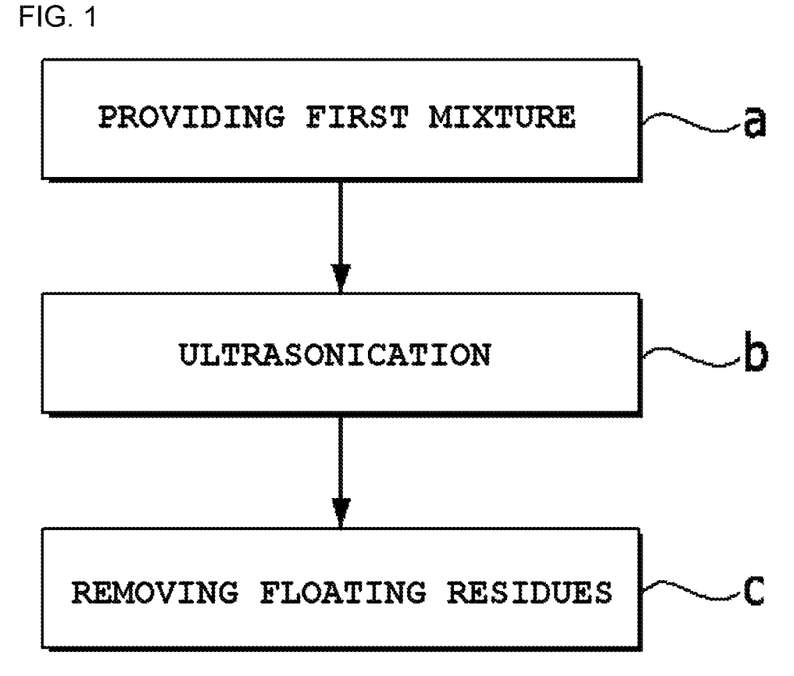
FIG. 1 is a flowchart schematically illustrating a process for a method for preparing a vegetable oil emulsion according to one embodiment of the present invention.

FIG. 1 is a flowchart schematically illustrating a process for a method for preparing a vegetable oil emulsion according to one embodiment of the present invention.

Referring to FIG. 1, the method for preparing a vegetable oil emulsion according to one embodiment of the present invention includes mixing water with a vegetable oil to provide a first mixture (a) and applying ultrasonic waves with a frequency of 25 to 70 kHz to the first mixture to solubilize the first mixture (b).

The water used for preparation of the vegetable oil emulsion according to the present invention may be deionized water.

Meanwhile, as shown in FIG. 1, a method for preparing a vegetable oil emulsion according to another embodiment of the present invention may further include removing some floating matter present in an upper layer of the emulsion (c), after (b).

Advantageously, the preparation method according to the present invention can be widely applied to various herbal oils for general use.

The preparation method according to the present invention can be carried out using a cleaning device through ultrasonication, for example, SonicPLUS commercially available from Samwoo SP Co., Ltd.

Hereinafter, the method for preparing a vegetable oil emulsion according to one embodiment of the present invention will be described in more detail with reference to FIGS. 2 to 8.

Figure 2:
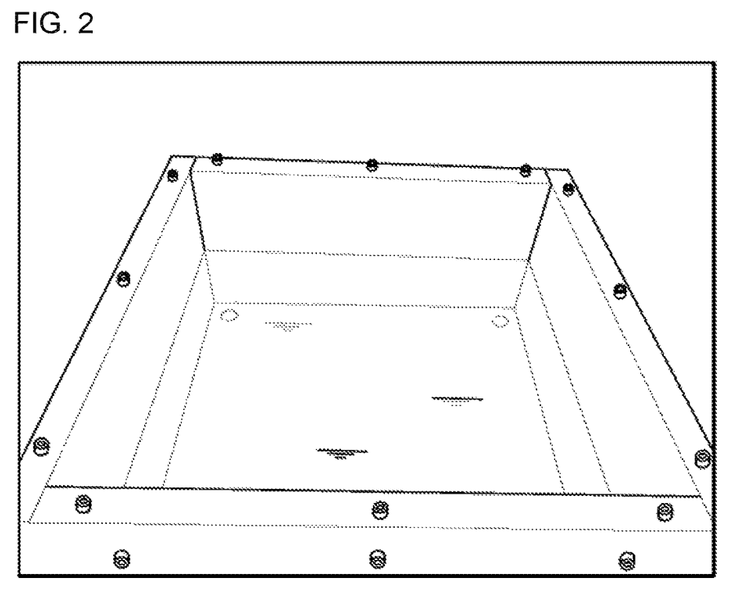
FIGS. 2 to 10 are images schematically showing a process for mixing lavender oil with water and conducting aqueous emulsification through ultrasonication according to one embodiment of the present invention.

FIG. 2 is an image showing a cleaning bath of an ultrasonic cleaner that contains water.

The water used in the present invention is preferably deionized water when taking into consideration various application fields of final products as described above.

Figure 3:
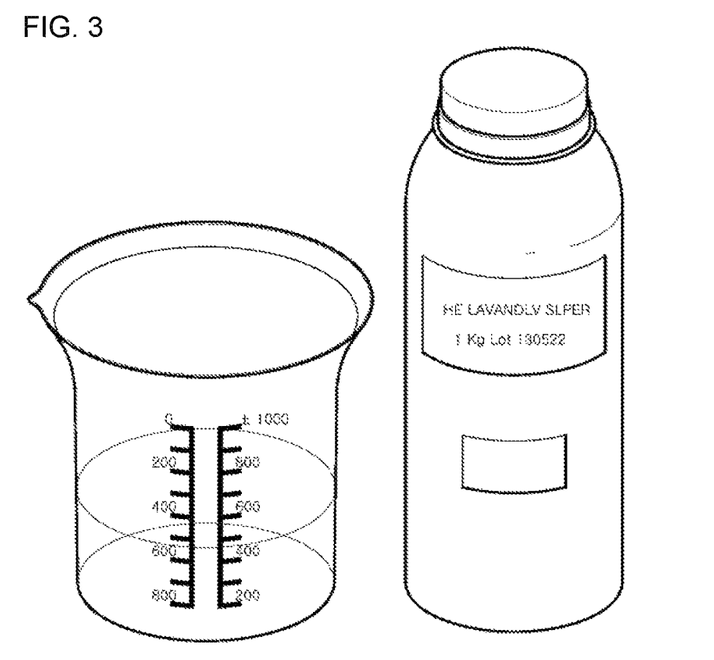

FIG. 3 is an image showing lavender oil (oil contained in a left beaker) that can be used in the preparation method according to one embodiment of the present invention.

The various vegetable oils such as herbal oils used in the present invention can be extracted with or without a solvent.

Examples of the method of extracting vegetable oils with a solvent include enfleurage, maceration, solvent extraction, carbon dioxide extraction and the like. Examples of the method of extracting vegetable oils without a solvent include expression process, steam distillation and the like.

Figure 4:
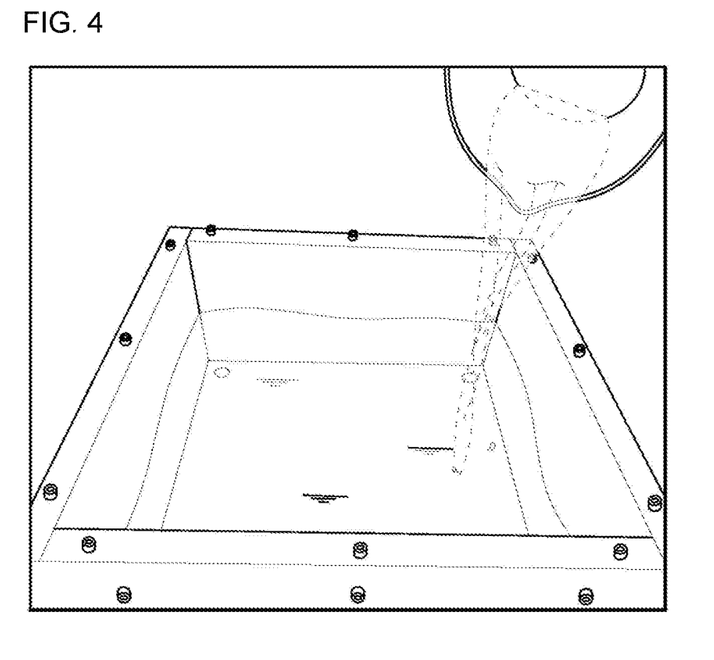

FIG. 4 is an image showing a process of preparing a first mixture by adding lavender oil to deionized water according to one embodiment of the present invention.

The mix ratio between water and the vegetable oil in the present invention can be changed depending on the vegetable oil mixed. For example, the vegetable oil is preferably mixed in an amount of 0.1 to 30 mL per 1 L of water.

When the amount of vegetable oil added is less than 0.1 mL, the final product almost cannot exert efficacies of vegetable oil and when the amount exceeds 30 mL, emulsion efficiency of oil and water is disadvantageously deteriorated due to ultrasonication.

Figure 5:
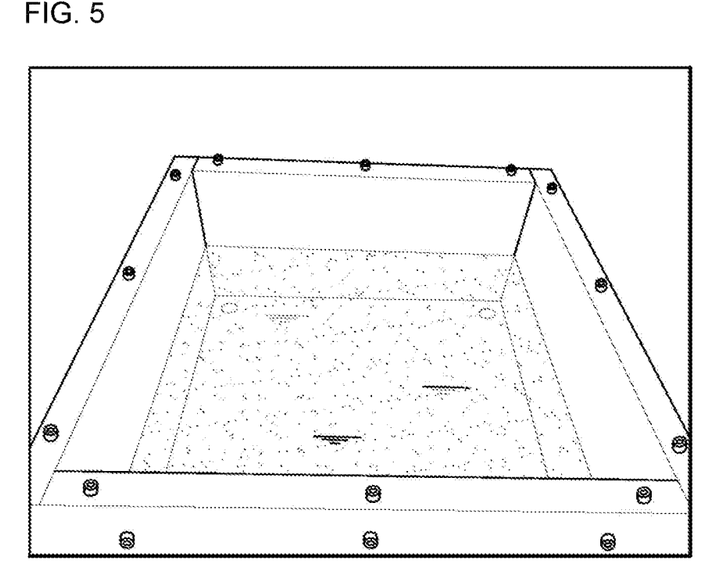
Figure 6:
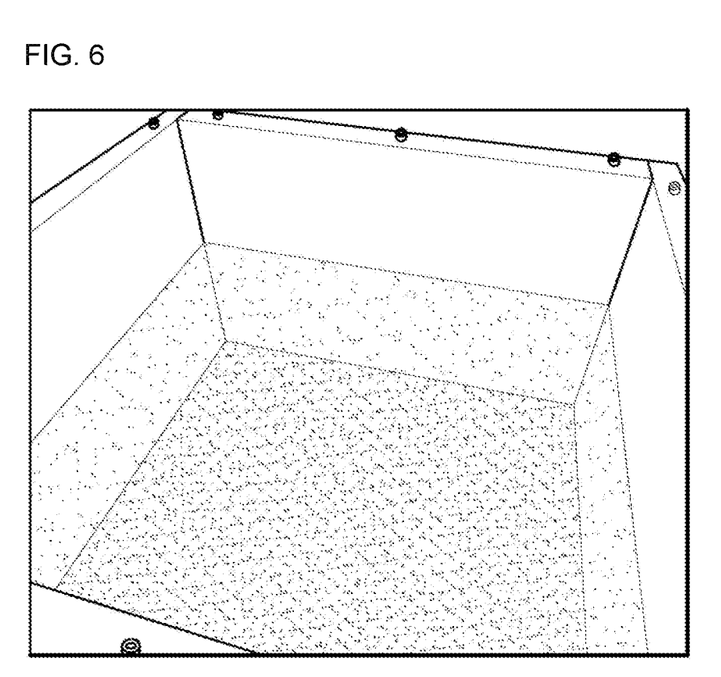

FIG. 5 is an image showing ultrasonication at an ultrasonic frequency of 40 kHz in an ultrasonic cleaner for 5 minutes, after adding the vegetable oil to water, as shown in 4, and FIG. 6 shows results of ultrasonication after 5 minutes.

As can be seen from FIG. 6, upon ultrasonication at an ultrasonic frequency of 40 kHz in an ultrasonic cleaner for 5 minutes, about 5% of added oil is solubilized.

Figure 7:
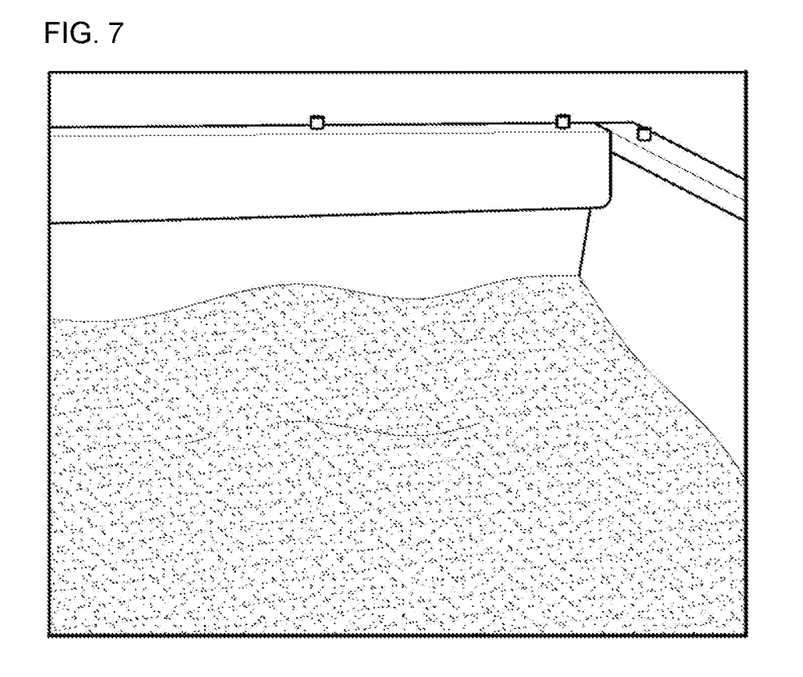

FIG. 7 is an image showing results of ultrasonication at an ultrasonic frequency of 40 kHz in an ultrasonic cleaner for 15 minutes. As can be seen from FIG. 7, about 15 to 20% of added oil is emulsified.

Figure 8:
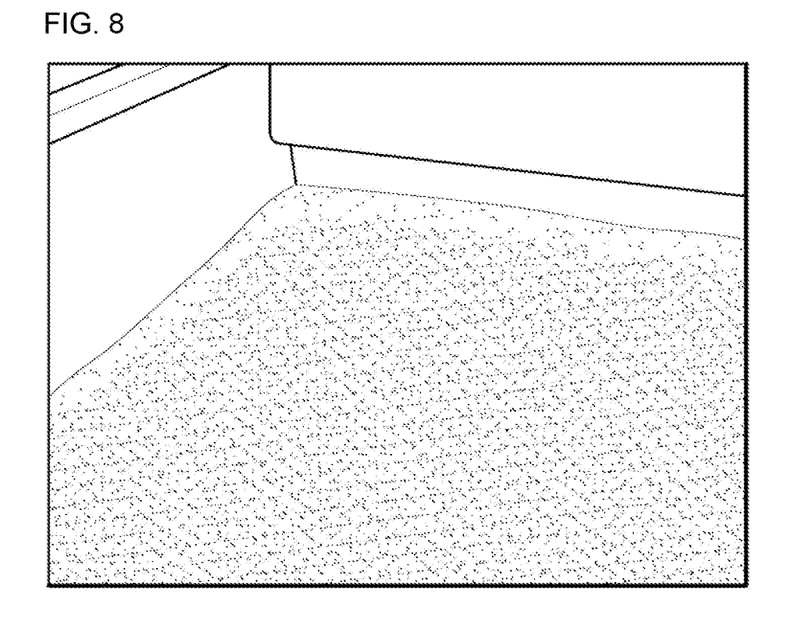

FIG. 8 is an image showing results of ultrasonication at an ultrasonic frequency of 40 kHz in an ultrasonic cleaner for 30 minutes. As can be seen from FIG. 8, about 30% of added oil is emulsified.

Figure 9:
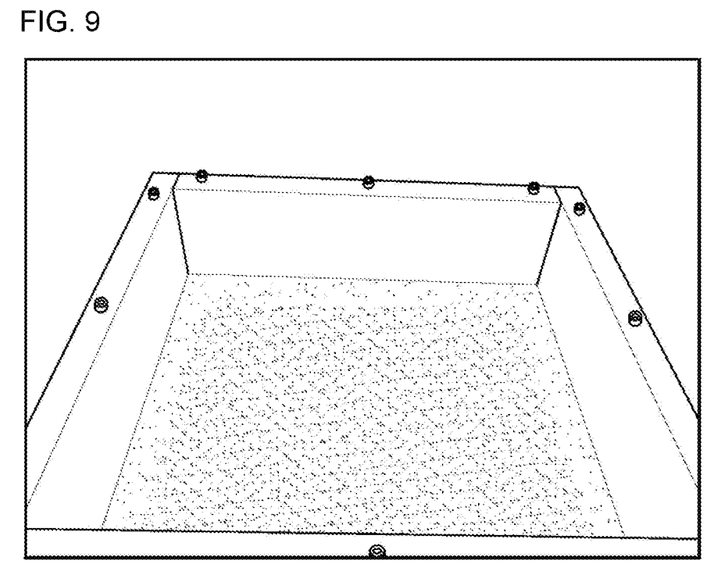

FIG. 9 is an image showing results of ultrasonication at an ultrasonic frequency of 40 kHz in an ultrasonic cleaner for one hour. As can be seen from FIG. 9, about 60% of added oil is emulsified.

Figure 10:
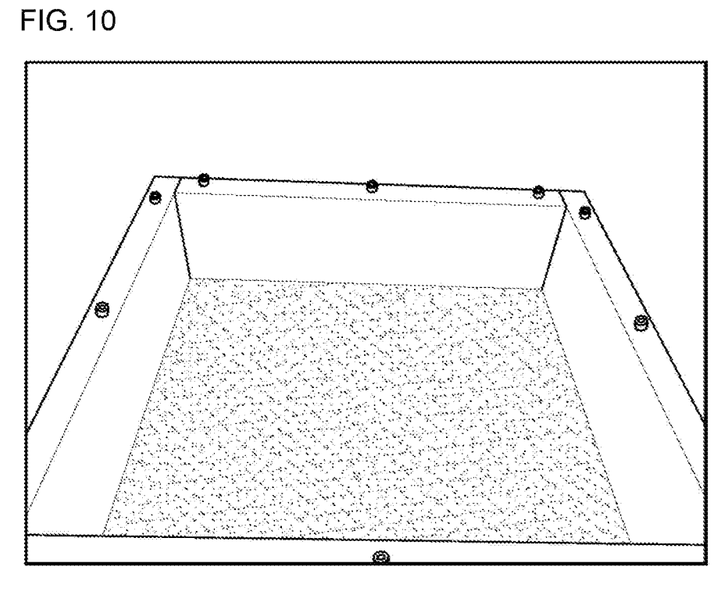
Figure 11:
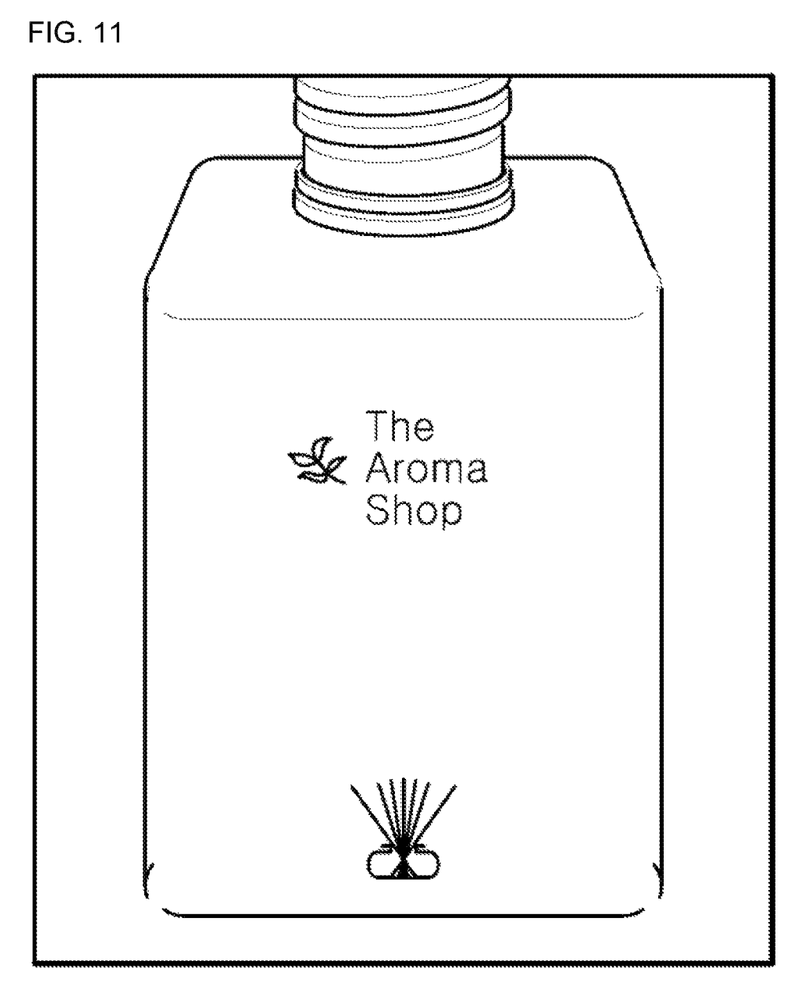
FIG. 11 is an image showing a sample which is aqueous-emulsified from lavender oil according to one embodiment of the present invention.
Figure 12:
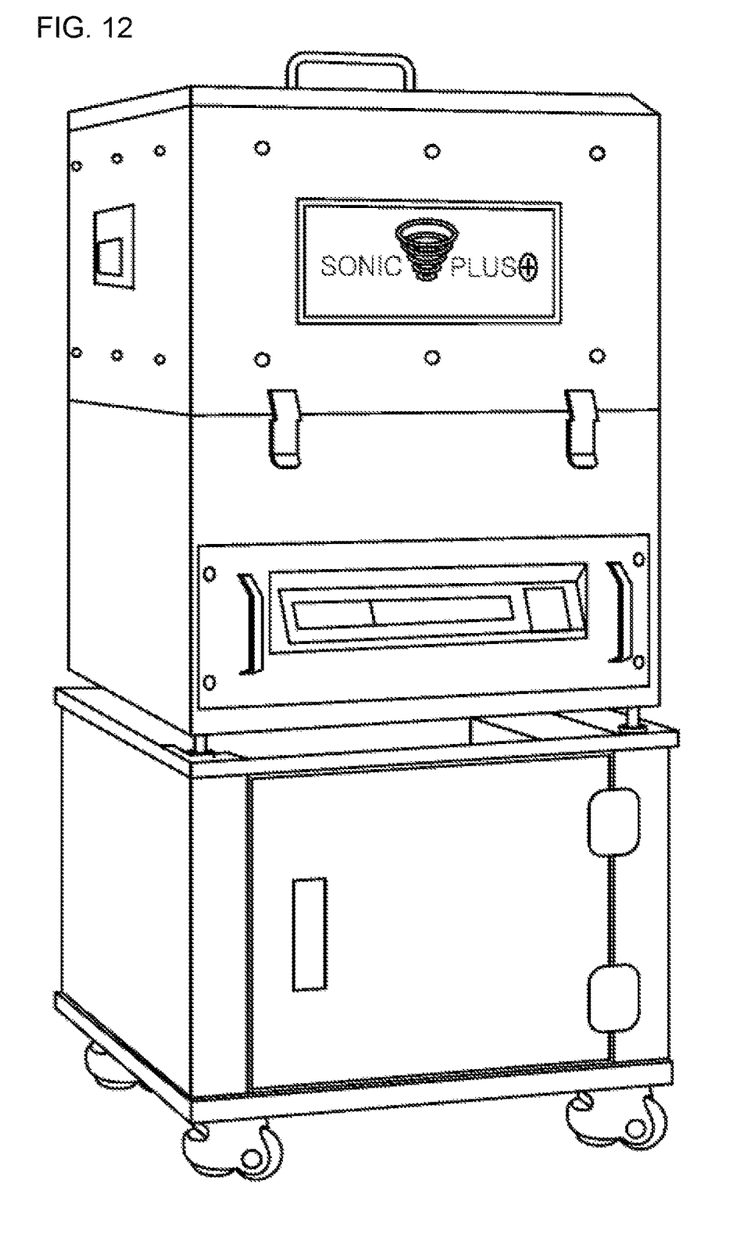
FIG. 12 is an image showing an ultrasonic cleaner commercially available from Samwoo SP Co., Ltd, that can be used in the preparation method according to one embodiment of the present invention.

FIG. 10 is an image showing results of ultrasonication at an ultrasonic frequency of 40 kHz and at 50° C. in an ultrasonic cleaner for 2 hours. As can be seen from FIG. 10, most of added oil is emulsified. At this time, a real operation temperature was about 60° C. due to an about 10° C. increase in temperature resulting from ultrasonication.

In regard with the method for preparing a vegetable oil emulsion according to another embodiment of the present invention, step (b) can be carried out by maintaining the temperature of the first mixture at 20 to 80° C.

When the temperature of ultrasonication is less than 20° C., emulsification efficiency may be deteriorated and, when the temperature exceeds 80° C., the oil may be denatured due to high-temperature operation, which may leave floating residues on the final product, deteriorate fragrance of the emulsion and allow the oil to be evaporated and lost.

With regard to the method for preparing a vegetable oil emulsion according to another embodiment of the present invention, step (b) can be carried out for 10 minutes to 8 hours, preferably 1 to 3 hours, more preferably 2 hours.

Meanwhile, with regard to the method for preparing a vegetable oil emulsion according to another embodiment of the present invention, application of ultrasonic waves in step (b) can be carried out by regularly changing an oscillation frequency in order to prevent resonance.

That is, when treatment of ultrasonic wave is conducted in the process of preparing the vegetable oil emulsion, standing waves may be disadvantageously generated. In this case, an energy distribution that an ultrasonic waveform stands in an ultrasonic cleaning bath is shown.

Such a standing wave phenomenon is due to resonance resulting from the applied ultrasonic energy, which may rather significantly lead to deterioration in emulsification efficiency of oils.

Accordingly, in order to prevent generation of the standing wave and thereby improve emulsification efficiency of vegetable oil, it is preferable to prevent reaction and synthesis between travelling waves and reflective waves by continuously changing the oscillation frequency of applied ultrasonic waves.

With regard to the method for preparing a vegetable oil emulsion according to one embodiment of the present invention, the vegetable oil may include one or more selected from the group consisting of lavender oil, lemongrass oil, rosemary oil, rose oil, citronella oil, lemon oil, bergamot oil, cedarwood oil, tea tree oil, peppermint oil, eucalyptus oil, anise oil, juniper berry oil, carrot seed oil, clary sage oil, clove bud oil, mandarin oil, myrrh oil, basil oil, cypress oil, sandalwood oil, sweet orange oil, spearmint oil, cinnamon oil, ylang ylang oil, jasmine oil, geranium oil, chamomile oil, neroli oil, lime oil, rose geranium oil, rosewood oil, marjoram oil, thyme oil, pine oil, palmarosa oil, fennel oil, petitgrain oil, patchouli oil, frankincense oil or a combination thereof.

The following Table 1 shows results of testing to determine an emulsification efficiency (%) of an oil using lavender oil while changing ultrasonic frequency and temperature (test conditions: mixing 2 mL of lavender oil with 1L of deionized water, ultrasonication for 2 hours).

Meanwhile, the sample having an emulsification ratio of 950 or more was allowed to stand at 25° C. for 3 months and was further tested for the period of time until which the oil and water are layer-separated. Results are shown in the following Table 1 (the numbers written in parentheses represent days taken until layer-separation occurs) ("X" in parenthesis represents that layer-separation is not observed even after 3 months).

TABLE 1

|  | 15° C. | 20° C. | 30° C. | 40° C. | 50° C. | 60° C. | 80° C. | 82° C. | 85° C. |
|---|---|---|---|---|---|---|---|---|---|
| 0.5 kHz | 1 | 5 | 15 | 20 | 25 | 26 | 30 | 35 | 35 |
| 1 kHz | 2 | 6 | 18 | 22 | 30 | 32 | 35 | 38 | 41 |
| 5 kHz | 5 | 15 | 25 | 28 | 35 | 36 | 41 | 45 | 46 |
| 10 kHz | 8 | 16 | 28 | 30 | 38 | 39 | 44 | 52 | 57 |
| 20 kHz | 11 | 18 | 31 | 33 | 42 | 45 | 49 | 55 | 62 |
| 25 kHz | 15 | 95 | 95 | 95 | 95 | 96 | 98 | 98 | 98 |
|  |  | (X) | (X) | (X) | (X) | (X) | (X) | (12) | (8) |
| 40 kHz | 20 | 95 | 95 | 95 | 95 | 97 | 98 | 98 | 98 |
|  |  | (X) | (X) | (X) | (X) | (X) | (X) | (11) | (7) |
| 50 kHz | 25 | 95 | 95 | 95 | 95 | 98 | 99 | 99 | 99 |
|  |  | (X) | (X) | (X) | (X) | (X) | (X) | (12) | (6) |
| 60 kHz | 28 | 95 | 95 | 95 | 95 | 96 | 98 | 98 | 98 |
|  |  | (X) | (X) | (X) | (X) | (X) | (X) | (15) | (7) |
| 70 kHz | 30 | 95 | 95 | 95 | 95 | 98 | 99 | 99 | 99 |
|  |  | (X) | (X) | (X) | (X) | (X) | (X) | (14) | (8) |
| 75 kHz | 33 | 51 | 65 | 76 | 82 | 85 | 86 | 87 | 88 |
| 80 kHz | 40 | 55 | 68 | 81 | 82 | 85 | 87 | 88 | 88 |
| 90 kHz | 41 | 55 | 68 | 83 | 84 | 85 | 87 | 88 | 89 |

(Proportion of Emulsified Oil: %)

As can be seen from Table 1, when the ultrasonic frequency is adjusted to 25 to 70 kHz and the ultrasonication temperature is set to 20° C. or higher, the oil is emulsified at an efficiency of 95% or more.

Meanwhile, as can be seen from results of Table 1, when ultrasonication temperature is set to 20 to 80° C., layer-separation of the emulsion is not observed even after 3 months, but, when ultrasonication temperature is set to 82° C. or higher, the oil and water are layer-separated from each other after about 6 to 15 days.

In addition, at a ultrasonication temperature higher than 80° C., production of floating residues is observed.

Meanwhile, the present inventors conducted testing under the same conditions as in Table 1, using each of lemongrass oil, rosemary oil, rose oil, citronella oil, lemon oil, bergamot oil, cedarwood oil, tea tree oil, peppermint oil, eucalyptus oil, anise oil, juniper berry oil, carrot seed oil, clary sage oil, clove bud oil, mandarin oil, myrrh oil, basil oil, cypress oil, sandalwood oil, sweet orange oil, spearmint oil, cinnamon oil, ylang ylang oil, jasmine oil, geranium oil, chamomile oil, neroli oil, lime oil, rose geranium oil, rosewood oil, marjoram oil, thyme oil, pine oil, palmarosa oil, fennel oil, petitgrain oil, patchouli oil and frankincense oil. When these oils are used, substantially the same results as when lavender oil is used can be obtained.

That is, when these oils are used as well, treatment with 25 to 75 kHz ultrasonic waves at a temperature of 20 to 80° C. can provide emulsification of 95% or more and avoid layer-separation between the oil and water even after 3 months. At a temperature higher than 80° C., generation of floating residues is observed.

The invention claimed is:

1. A method for preparing a vegetable oil emulsion comprising:
   mixing water with a vegetable oil to provide a first mixture (a); and
   applying an ultrasonic wave with a frequency of 25 to 70 kHz to the first mixture to solubilize the first mixture (b),
   wherein the application of ultrasonic waves in the step (b) is carried out while regularly changing an oscillation frequency to prevent reaction and synthesis between a travelling wave and a reflective wave, in order to prevent deterioration in emulsification efficiency due to resonance,
   step (b) is carried out while maintaining a temperature of the first mixture at 20 to 80° C. to prevent layer-separation between the oil and water,
   the vegetable oil is lavender oil, lemongrass oil, rosemary oil, rose oil, citronella oil, lemon oil, bergamot oil, cedarwood oil, tea tree oil, peppermint oil, eucalyptus oil, anise oil, juniper berry oil, carrot seed oil, clary sage oil, clove bud oil, mandarin oil, myrrh oil, basil oil, cypress oil, sandalwood oil, sweet orange oil, spearmint oil, cinnamon oil, ylang ylang oil, jasmine oil, geranium oil, chamomile oil, neroli oil, lime oil, rose geranium oil, rosewood oil, marjoram oil, thyme oil, pine oil, palmarosa oil, fennel oil, petitgrain oil, patchouli oil or frankincense oil, and
   regarding the solubilized first mixture, 95 wt % to 99 wt % of the vegetable oil is emulsified regardless of the type of the oil, and layer-separation between the oil and water does not occur at a temperature of 25° C. even after 3 months.

2. The method according to claim 1, further comprising removing floating residues (c) after step (b).

3. The method according to claim 1, wherein the first mixture is obtained by mixing the vegetable oil in an amount of 0.1 to 30 mL per 1 L of water.

4. The method according to claim 1, wherein step (b) is carried out for 10 minutes to 8 hours.

* * * * *